United States Patent [19]

Kroll

[11] Patent Number: 4,672,977
[45] Date of Patent: Jun. 16, 1987

[54] LUNG SOUND CANCELLATION METHOD AND APPARATUS

[75] Inventor: Mark W. Kroll, Rogers, Minn.

[73] Assignee: Cherne Industries, Inc., Minneapolis, Minn.

[21] Appl. No.: 872,534

[22] Filed: Jun. 10, 1986

[51] Int. Cl.$^4$ ............................ A61B 5/02; A61B 7/00
[52] U.S. Cl. ...................................... 128/715; 128/644; 128/773
[58] Field of Search ............... 128/715, 773, 660, 639, 128/644, 714, 640, 668; 73/632; 179/132

[56] References Cited

U.S. PATENT DOCUMENTS

| | | | |
|---|---|---|---|
| 1,282,908 | 10/1918 | Miller | 128/715 X |
| 3,525,810 | 8/1970 | Adler | 128/715 |
| 3,762,397 | 10/1973 | Cage | 128/700 |
| 3,921,623 | 11/1975 | Okada et al. | 128/715 X |
| 3,985,121 | 10/1976 | Hellenbrand | 128/689 |
| 4,048,986 | 9/1977 | Ott | 128/660 X |
| 4,122,843 | 10/1978 | Zdrojkowski | 128/644 |
| 4,194,510 | 3/1980 | Proudian | 128/660 |
| 4,220,160 | 9/1980 | Kimball | 128/715 |
| 4,378,022 | 3/1983 | Suobank | 128/715 |
| 4,428,380 | 1/1984 | Wong | 128/715 |
| 4,438,772 | 3/1984 | Slavin | 128/715 |
| 4,559,953 | 12/1985 | Wright et al. | 128/715 X |

Primary Examiner—Kyle L. Howell
Assistant Examiner—Angela D. Sykes
Attorney, Agent, or Firm—Anthony G. Eggink

[57] ABSTRACT

A method and apparatus for deriving weak cardiac sounds by automatically cancelling lung sounds. The process is accomplished by providing a pair of acoustic sensors about the thorax of a patient, the first being disposed on the precordial region, adjacent to the sternum, and the second on the axillary region; obtaining sound signals from each sensor; amplifying the axillary signal by a predetermined factor; and subtracting the amplified signal from the precordial signal. An acoustic transmitter is placed on the axillary region opposite the axillary sensor. Sound waves of predetermined frequencies are emitted from the axillary transmitter to determine and compensate for phase shifts due to the electronic circuitry and the patient body. The apparatus of the present invention comprises a first acoustic sensor, a second acoustic sensor, an acoustic transmitter, a strap, transmitting cables, a processor, a cathode-ray tube, a printer, and headphones.

17 Claims, 6 Drawing Figures

LUNG SOUND CANCELLATION METHOD AND APPARATUS

BACKGROUND OF THE INVENTION

This invention relates to phonocardiographic analysis and, more particularly, to analysis of weak cardiac sounds.

It has long been recognized that heart sound identification is an important tool in diagnosing cardiac disease. A variety of methods have been, and are presently, used to detect and analyze heart sounds. The stethoscope allows a physician to listen directly to heart sounds. These sounds may also be amplified by electronic means. However, the weaker heart sounds, which primarily result from abnormal hemodynamic function, diastolic murmurs, coronary stenotic murmurs and the like, are often masked by respiration sounds. Accordingly, various methods have been proposed or used to separate or distinguish these weaker heart sounds from breathing sounds.

One such technique involves computer averaging of electrocardiographic signals without regard to synchronization of breathing. Although it is useful to eliminate undesirable noise waveforms to accentuate specific heart sound components, the resolution of weak sounds is sacrificed. Another resolution technique utilized involves having a patient hold his breath while the researcher or practitioner analyzes, by conventional means, a number of heart beats, such as five beats for example. This procedure is repeated until approximately two hundred heart beats have been analyzed. This method is uncomfortable for the patient and is inconvenient and burdensome for the technician.

The object of the present invention is to provide a method for quickly, easily and accurately distinguishing sounds generated by cardiac functions from breathing sounds. It is a further object of this invention to provide a method to quickly and accurately detect and display for subsequent diagnosis a broad range of heart sounds, particularly weak heart sounds. Another object of the present invention is to provide a means to distinguish sounds generated by cardiac function from breathing sounds. It is a further object of this invention to provide a means to quickly and easily detect, isolate and display a broad range of heart sounds, particularly weak heart sounds. And, although a need exists in the medical diagnostic art for such methods and means, none insofar as is known has been proposed or developed.

SUMMARY OF THE INVENTION

The present invention is a method and apparatus for deriving weak cardiac sounds by the automatic cancellation of lung sounds. The process is accomplished by providing a pair of acoustic sensors about the thorax of a patient, one being disposed on the cardiac region and the other on an axillary region; obtaining sound signals from each sensor; amplifying the axillary sensor signal by a predetermined factor; and subtracting the amplified signal from the cardiac sensor signal. An acoustic transmitter is placed on the axillary region opposite the axillary sensor. Sound waves of predetermined frequencies are emitted from the axillary transmitter to determine and compensate for electronic phase shifts.

The apparatus of the present invention comprises a first acoustic sensor, a second acoustic sensor, an acoustic transmitter, securement means, cable means, a processing means, a cathode-ray tube (CRT), a printer, and headphones. The acoustic sensors and transmitter are placed on predetermined areas of the patient body. The sensors detect thoracic bio-acoustic signals which are processed to yield a true heart sound signal which is free of respiration sounds. Sound waves of predetermined frequencies are emitted from the acoustic transmitter to determine and compensate for electronic phase shifts.

These and other benefits of this invention will become clear from the following description, by reference to the drawings.

DESCRIPTION OF THE PREFERRED EMBODIMENT

Figure 1:
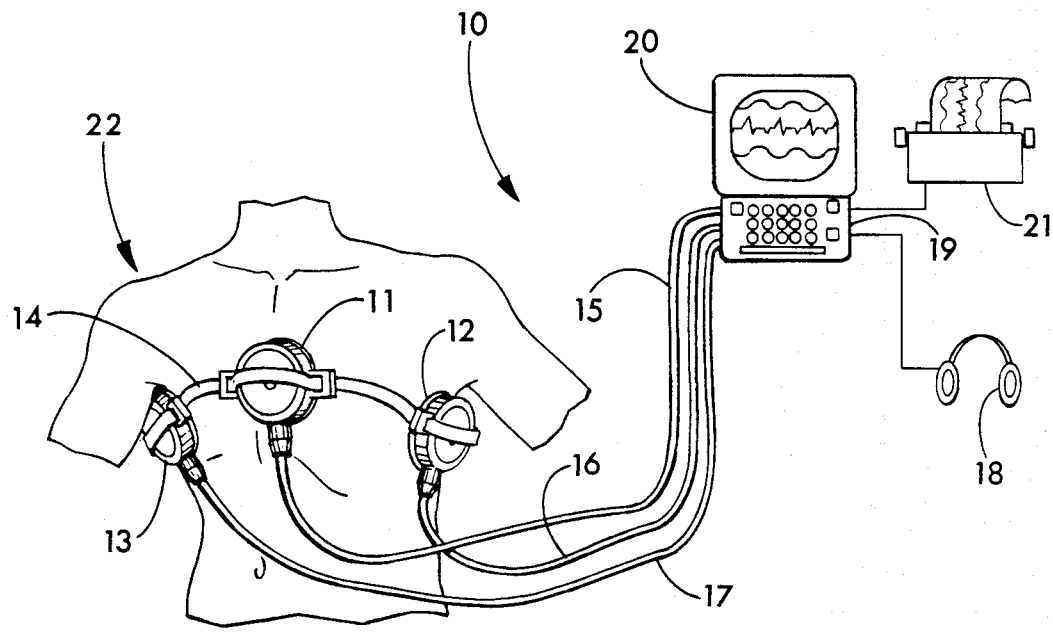
FIG. 1 shows the apparatus of the present invention with its sensing and transmitting elements in an operative position on the body of a patient.
Figure 6:
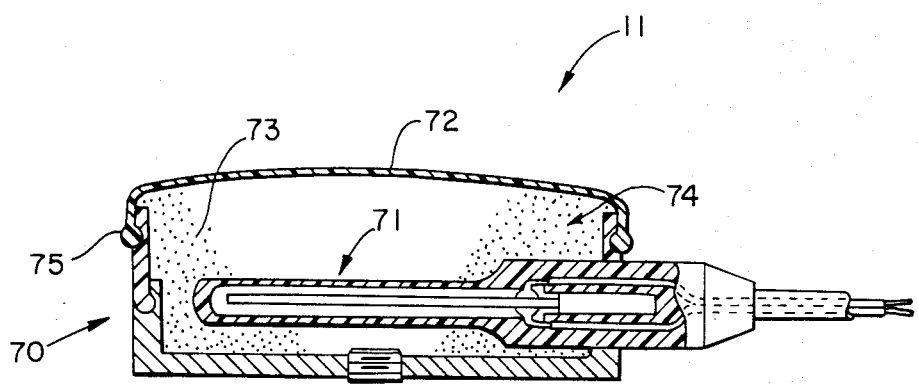
FIG. 6 is a cross-sectional view of the heart sound sensors shown in FIGS. 1 and 2.

Referring to FIG. 1, the lung sound cancellation apparatus 10 of the present invention is shown in use on a patient 22. It comprises a first acoustic sensor 11, a second acoustic sensor 12, an acoustic transmitter 13, strap means 14, transmitting cable means 15, 16, and 17, an electronic analyzer or processing means 19, a display means or cathode-ray tube (CRT) 20, a printer 21 and headphones 18. The first acoustic sensor 11 is for detecting or receiving bio-acoustic signals from patient 22. The sensor 11 is preferably of a design described in a co-pending U.S. patent application filed by Mark W. Kroll for a Heart Sound Sensor. Referring to FIG. 6, such a heart sound sensor 11 has a housing structure 70, a hydrophone 71, a flexible diaphragm 72 and a fluid medium 73. The housing structure has an open end 74 for reception of sound waves. The hydrophone 71 is disposed in the housing structure 70. It produces electrical signals in response to transmitted sound waves. The flexible diaphragm 72 extends across the open end 74 of the housing structure 70 and has a retainer 75 which holds it in this position. The diaphragm 72 is placed in direct contact with the patient. The fluid medium 73 fills the interior of the housing structure 70 and transmits sound waves from the diaphragm 72 to the hydrophone 71. Alternatively, the sensor 11 may be of a different design known in the phonocardiographic art, capable of detecting heart sounds in the general frequency range of 1000 to 2000 Hz. These designs typically utilize a transducer or microphone. The first acoustic sensor 11 produces an output electrical signal in response to input sound waves generated by the heart, lungs and the acoustic transmitter 13. Variations in the output signal are a function of the input sound waves. The first acoustic sensor 11 is placed at a predetermined location, generally centered at the sternum, on the chest of patient 22.

The second acoustic sensor 12, which is preferably identical to sensor 11, is for receiving sound waves generated by the heart, lungs and the acoustic transmitter 13. It is placed at a predetermined location, generally below the armpit, on the axillary region of the patient 22. The acoustic transmitter 13 is for transmitting output sound waves of specified frequencies in response to input electrical signals. It is an electroacoustic transducer of a design commonly known in the echocardiographic art. The acoustic transmitter 13 is disposed at a predetermined location, opposite the second acoustic sensor 12, on the axillary region of patient 22.

The acoustic sensor 12 and acoustic transmitter 13 may alternatively be of the design having a bilateral transducer. Therefore, either device is usable to detect sound waves from their respective axillary locations and usable to transmit sound waves. This configuration provides further operator control of axillary sound signal detection by permitting operator choice based upon clinical considerations.

The above-mentioned sensors 11, 12 and transmitter 13 are held in place at their predetermined locations about the thorax of patient 22 by strap means 14. The strap means 14 is generally a flexible strip or band which adjustably engages sensors 11 and 12 and transmitter 13 and which has fastening means to secure these elements to the thorax of patient 22. The first acoustic sensor 11 is communicatively connected to the processing means 19 by cable means 15. The second acoustic sensor 12 and acoustic transmitter 13 are similarly linked with processing means 19 by cable means 16 and cable means 17 respectively.

The processing means 19 is an electronic data processing system having processing circuitry and an operator keyboard. It receives and analyzes electrical signals from the first acoustic sensor 11 and from the second acoustic sensor 12. Processing means 19 additionally produces electrical signals for transmission to the acoustic transmitter 13. The processing means 19 is communicatively connected to the CRT or display means 20, the printer 21, and to headphones 18.

Figure 2:
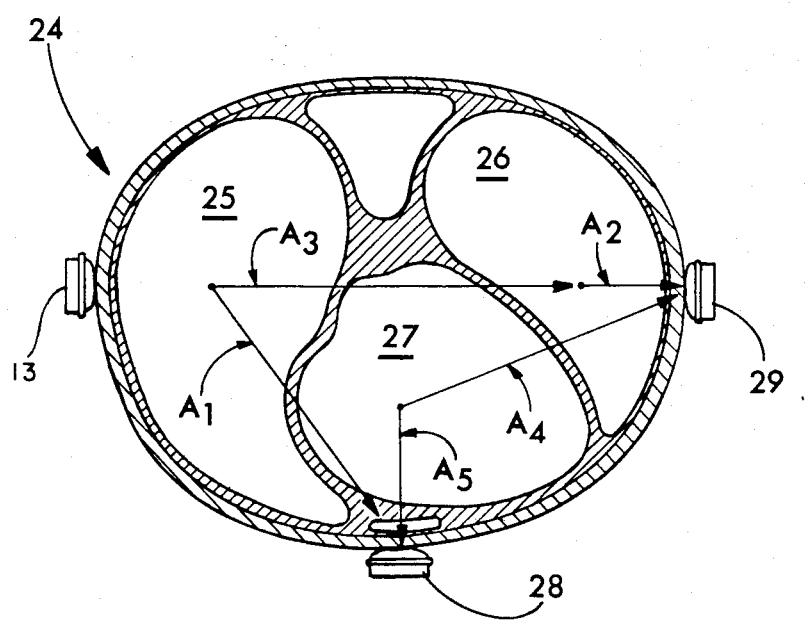
FIG. 2 is a view in cross-section of a thoracic acoustical model which represents the patient body shown in FIG. 1 at approximately the lower rib area and which is useful in explaining the apparatus and methods of the invention.

Referring to FIG. 2, a patient thoracic acoustical model 24 is shown having lungs 25, 26 and a heart 27. It generally represents a cross-section of a human patient thorax at the lower rib area. The method of the present invention involves placing a pair of acoustic sensors 28 and 29 about the thorax at predetermined locations. One sensor 28 is placed on the precordial region, adjacent to the heart 27. The second sensor 29 is placed in an axillary location.

Each sensor 28, 29 detects lung sounds (L) from each lung 25 and 26 respectively. Additionally, each sensor 28, 29 senses heart sounds (H) generated by the heart 27. However, the sound signal received at either sensor 28, 29 is not the true sound wave from the heart 27 (H) and lungs 25, 26 (L), but is in essence an attenuated wave therefrom. The attenuation or weakening of the true sound wave is primarily due to dissipation of acoustic energy from heart 27 and lung 25, 26 sounds (H, L), and can be divided into two general categories: (1) that due to losses in the tissue medium itself and (2) losses at the boundaries of the tissue media. This latter type of loss is due to sound wave reflection caused when acoustic waves traveling in one medium encounter the boundary of a second medium.

The former category, losses within the tissue media, can be further divided into absorption mechanisms that convert acoustic energy into thermal energy and deflection mechanisms that scatter energy out of the sound wave. When a medium contains inhomogeneities such as suspended particles, gas bubbles or regions of varying density, acoustic energy is lost from a sound wave faster than in a homogeneous medium. Therefore, high attenuations are produced in the lungs 25 and 26 because of such inhomogeneities. For instance, viscous and heat conduction losses associated with the compression and expansion of tissue and gas chambers by a passing sound wave result in a loss of energy by the sound wave. These losses are characterized as absorption. Scattering is also caused by inhomogeneous media. And, scattering further decreases the energy of the sound wave. Thus, attenuation due to absorption and reflection occurs both within the heart 27 and lungs 25, 26 tissue media and also between their tissue boundaries.

For purposes of deriving the true heart sounds, for use in the method of this invention, the attenuation factors for the heart 27 sounds (H) and the lungs 25 and 26 sounds (L) are represented by the coefficient or parameter "Aj", where j ranges from 1 to 5. Sound generated by lung 25 (L) is transmitted to both sensor 28 and sensor 29. Attenuation of transmission occurs as a result of the tissue of lung 25 itself, heart 27 tissue and lung 26 tissue. Sound generated by lung 26 (L) is also transmitted to both sensors 28 and 29. Attenuation, therefore, occurs as a result of lung 26 tissue as well as heart 27 tissue. Finally, sound generated by heart 27 (H) and transmitted to both sensors 28, 29 is attenuated by its own tissue and also by that of lung 26.

Referring to FIGS. 1 and 2, the heart 27 and lungs 25, 26 generate sound in the frequency range of 100 to 1000 Hz. For these frequencies, the sound wavelength in the body is greater than 1 meter and thus, there is a relatively constant phase throughout the thorax. If there are no electronic phase shifts, the total signal detected by the cardiac sensor 28 ($E_C$) can be represented by $$E_C = A_5 H + 2 A_1 L$$

where
$A_1$ is the acoustic transmission coefficient from lung 25 and lung 26 to sensor 28, and
the system is normalized so that the transmission coefficient from heart 27 to sensor 28 ($A_5$) is 1.0.

Similarly, the signal detected by the axillary sensor 29 ($E_A$) is given by $$E_A = A_4 H + A_2 L + A_2 A_3 L$$

where
$A_2$ is the acoustic transmission coefficient from lung 26 to sensor 29,
$A_3$ is the acoustic transmission coefficient from lung 25 to lung 26, and
$A_4$ is the acoustic transmission coefficient from heart 27 to sensor 29.

Using the two equations above, the heart sound (H) is given by $$H = \frac{1}{G_1} E_C - \frac{1}{G_1} \left[ \frac{2 A_1}{(1 + A_3) A_2} \right] E_A$$

-continued $$\text{where } G_1 = 1 - \frac{2 A_1 A_4}{(1 + A_3)A_2}$$

It is also known that $$G_1 \neq 0$$

and is therefore invertible.

Now, letting $H_S$ be the "synthesized" heart sound and defining $$H_s = G_1 H$$

then, $$H_S = E_C - G_2 E_A$$

where $$G_2 = \frac{2A_1}{(1 + A_3)A_2}$$

The synthesized heart sound is found by multiplying the axillary signal ($E_A$) by a constant ($G_2$) and subtracting the product from the cardiac signal ($E_C$). Thus, by simultaneously determining the overall thoracic acoustical signal from both a precordial position ($E_C$) and an axillary position ($E_A$), it is possible, in accordance with the invention, to determine the true heart sound (H), including weaker components thereof, free from lung sound (L) interference.

Defining the transmission coefficient for half of lung 25 or full lung 26 as $\alpha$ and assuming that $\alpha$ is very small, for example, approximately zero, then $$G_2 = \lim_{\alpha \to 0} \frac{2\alpha}{\alpha + \alpha^3}$$

$$= 2$$

Assuming $\alpha$ is very large, for example, approximately one half, then $$G_2 = \frac{2 \cdot \frac{1}{2}}{\frac{1}{2} + (\frac{1}{2})^3}$$

$$= 1.6$$

Hence, $$1.6 < G_2 < 2$$

Figure 3:
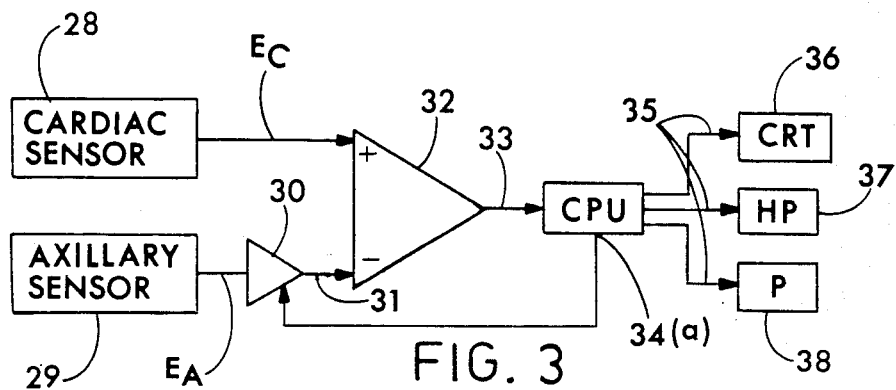
FIG. 3 is a schematic flow diagram of the method of the invention.

Referring to FIG. 3, the invention provides a method of deriving weak sounds generated by the heart by cancelling breathing sounds. An acoustic sensor 29 is placed in the axillary region on the thorax of a patient. Another acoustic sensor 28 is placed on the precordial region of the patient, adjacent to the sternum. Input thoracic sound signals are received by each sensor 28, 29. The output electrical signal ($E_A$) from sensor 29 is amplified 30 by a predetermined factor of between 1.6 and 2.0. The amplified signal 31 is then subtracted 32 from the output signal ($E_C$) of sensor 28. The subtracted output signal 33 is analyzed 34(a) to adjust the amplification step 30 to obtain an optimal heart sound signal 35, free of breathing sounds. Signal 35 is then visually displayed 36 and aurally monitored 37. The output signal 35 may also be printed 38.

Figure 4:
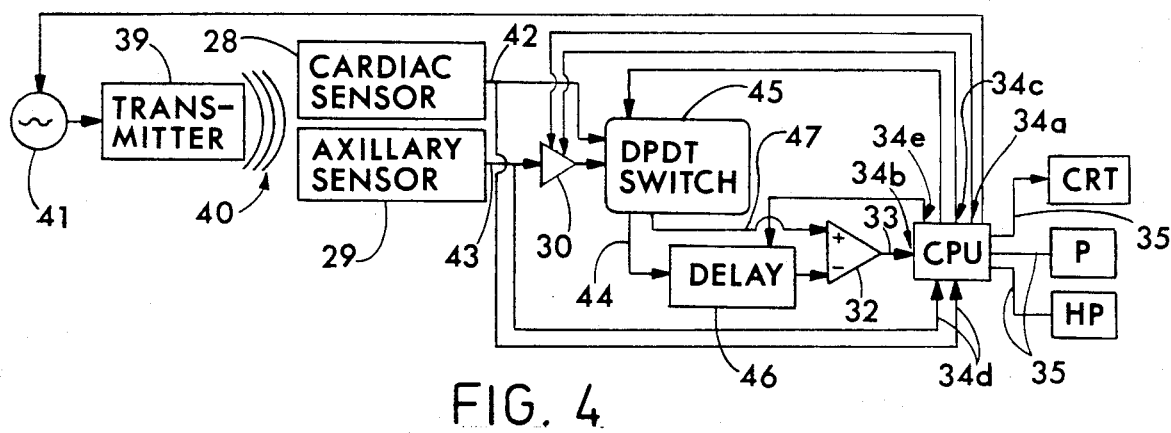
FIG. 4 is a schematic flow diagram of the method of the invention which shows the electronic phase shift calculation and correction steps.

For bio-acoustic signals, the sound wavelength in the body is greater than 1 meter and thus, there is a relatively constant phase in the thoracic cavity. However, there may be phase shifts in the transducer and remaining electronic circuitry. The overall electronic phase shift between sensors is measured and compensated for by the following steps. Referring to FIG. 4, the subtracted output signal 33 may contain a phase difference. The phase difference is detected by analysis 34(b). An acoustic transmitter 39 is placed on the axillary region opposite sensor 29. Amplification 30 is automatically set 34(c) at 1.0 and sound waves 40 are generated by transmitter 39 at frequencies of interest via oscillation 41. These frequencies generally correspond to heart sound frequencies, for example, 100 to 1000 Hz.

The next step involves reception of the sound waves 40 by sensors 28 and 29. Output signals 42 and 43 from each sensor 28 and 29 are analyzed 34(d) to determine which signal 42 or 43 is earlier. The earlier signal 44 is switched 45 and delayed 46. Different frequencies are cycled from transmitter 39 via oscillation 41 and analyzed 34(e) to adjust the delay step 46 for the best match between the earlier signal 44 and the later signal 47.

The final steps involve termination of oscillation 41 and reception of thoracic sounds to derive $E_A$ and $E_C$. Adjustment 34(a) is made of the amplification 30 until a clear heart sound signal 35, free from breathing sounds, is obtained. Adjustment 34(a) of amplification 30 to determine $G_2$ is done automatically as a function of frequency by the above-described phase correction method. Adjustment 34(a) may alternatively be made by the operator. A skilled operator apprised of particular body attenuation factors can determine when a clear signal 35 is being analyzed.

Referring again to FIG. 1, the apparatus 10 of the invention comprises an acoustic sensor 11 which is placed adjacent to the sternum of a patient 22 and a second sensor 12 which is placed in an axillary position below the armpit. Signals obtained simultaneously from sensors 11 and 12 are processed by processing unit 19 in accordance with the equation $$H_S = E_C - G_2(E_A)$$

where $$1.6 < G_2 < 2;$$

$E_C$ is the sound signal received from sensor 11; and
$E_A$ is the sound signal received from sensor 12.

Figure 5:
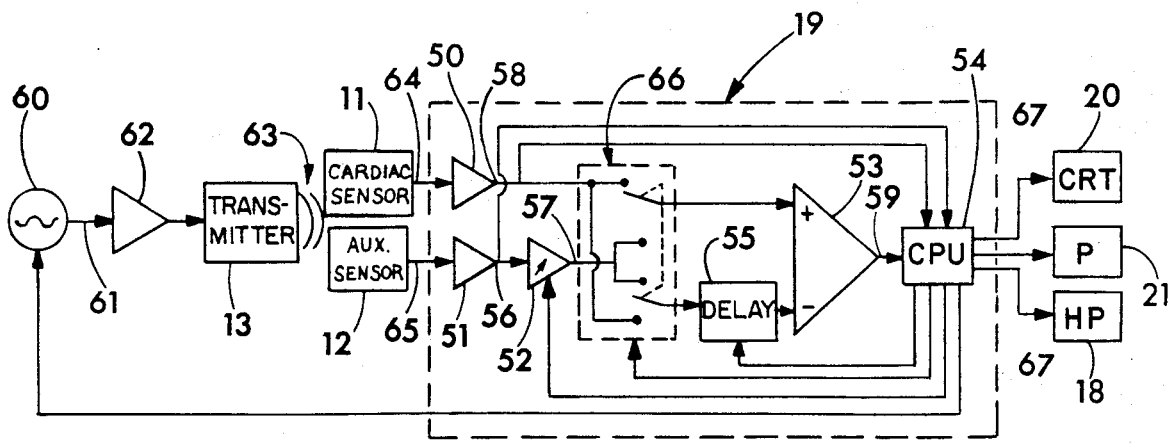
FIG. 5 is a schematic flow diagram of the apparatus in accordance with the invention.

As is shown in FIG. 5, processing unit 19 has a pair of pre-amplifiers 50, 51, an amplifier 52, a differential amplifier 53 and a microprocessor 54. Microprocessor 54 is a central processing unit of a design known in the art. It has an arithmetic and logic unit, storage and associated registers, and controls. Pre-amplifiers 50, 51 increase the voltage of output signals $E_C$ and $E_A$, of sensor 11 and sensor 12 respectively, by an equivalent predetermined amount. Amplifier 52 is a variable gain amplifier which increases the voltage of output signal 56 of pre-amplifier 51 by a predetermined factor ranging from 1.6 to 2.0, the derivation of which is described above. The amplification factor ($G_2$) is automatically adjustable by the microprocessor 54 to obtain a clear heart sound 67. Additionally, the operator may manually adjust the amplifier 52. Differential amplifier 53 subtracts the amplified output signal 57 of amplifier 52 from the output signal 58 of pre-amplifier 50.

The device 10 further has elements which are used to calculate and correct electronic phase shifts. Microprocessor 54 analyzes the output signal 59 from the differential amplifier 53 to determine the range of frequencies required for phase shift calculation. An oscillator 60 cycles through the range of frequencies selected by the microprocessor 54. The oscillator output 61 is amplified by a preamplifier 62 and fed into the acoustic transmitter 13 which transmits corresponding acoustic waves 63 to the patient. The transmitted sound waves 63 are detected by both sensors 11 and 12. The microprocessor 54 determines which sensor 11 or 12 first produces output electrical signals 64 and 65 respectively, in response to the sound waves 63.

Microprocessor 54 normalizes amplifier 52 to 1.0. The microprocessor 54 then electronically shunts the earlier signal 64 or 65, via a double pole-double throw switch 66, to a delay network 55. The delay network 55 holds the earlier signal 64 or 65 for the requisite time period, as determined by the microprocessor 54, to bring them in phase with the later generated signal 64 or 65. The delay network 55 is preferably an all-pass filter system. With the delay network 55 properly adjusted for the best match between signals 64 and 65, the microprocessor 54 terminates oscillation.

Sensors 11, 12 receive thoracic acoustical signals to derive $E_C$ and $E_A$. The gain of amplifier 52 is adjusted, either automatically by the microprocessor 54, or manually by the operator, to set $G_2$. The apparatus is run to obtain a clear heart sound signal free from respiration sounds 67. Heart sound signal 67 is then visually displayed on the CRT 20. Audio reproduction of the signal 63 is accomplished by the headphones 18. A hard copy of the signal 63 is also made by the printer 21.

As many changes are possible to the embodiments of this invention utilizing the teachings thereof, the descriptions above, and the accompanying drawings should be interpreted in the illustrative and not the limited sense.

That which is claimed is:

1. A method for deriving low and high frequency heart sounds comprising the steps of:
   a. detecting first and second acoustic signals from the thorax of a patient, said first acoustic signal being obtained from the cardiac region and said second acoustic signal being obtained from an axillary region;
   b. converting said first and said second acoustic signals to respective first and second output electrical signals;
   c. automatically amplifying said second output electrical signal by a predetermined factor;
   d. subtracting said amplified signal from said first output signal to thereby obtain a heart sound signal free of lung sounds;
   e. detecting a phase difference in said output electrical signals by transmitting sound waves of predetermined frequencies into the patient, receiving said transmitted sound waves at the cardiac region and the axillary region, and producing electrical signals in response thereto; and
   f. compensating for said phase difference by delaying said output electrical signal from the region which first produces an electrical signal in response to said transmitted sound waves to correspond with said output electrical signal from the second region.

2. The method of claim 1, wherein said predetermined factor ranges in value from 1.6 to 2.0.

3. The method of claim 1, including the step of automatically adjusting said predetermined factor to obtain a clear heart sound signal.

4. The method of claim 1, including the step of display in the heart sound signal for operation diagnosis.

5. A method for cancelling breathing sound components of thoracic bio-acoustic signals to yield an accurate heart sound signal comprising:
   a. providing a first acoustic sensor at a predetermined location on the cardiac region of a patient;
   b. providing a second acoustic sensor at a predetermined location on the axillary region of the patient;
   c. providing an acoustic transmitter at a predetermined location on the axillary region of the patient opposite said second acoustic sensor;
   d. transmitting sound waves of predetermined frequencies, between 100 and 1,000 Hz, from said acoustic transmitter into the body of the patient, receiving said transmitted sound waves with said first and said second acoustic sensors, and producing electrical signals in response thereto;
   e. compensating for electronic phase shifts at said first and said second acoustic sensors by determining at which said acoustic sensor said electrical signals are first produced, and by delaying the electrical response from said sensor at which said electrical signals are first produced, to correspond with the other sensor;
   f. receiving input thoracic sound waves at said first and said second acoustic sensors to produce a corresponding output electrical signal for each said sensor;
   g. automatically multiplying the output electrical signal from said second acoustic sensor by a predetermined factor ranging from 1.6 to 2.0 by means of a variable gain amplifier to produce a multiplied output signal;
   h. subtracting said multiplied output signal from the output electrical signal from said first acoustic sensor by means of a differential amplifier to produce a subtracted output signal; and
   i. displaying said subtracted output signal for operator diagnosis by means of a cathode-ray tube, a printer and headphones.

6. The method of claim 5, including the step of automatically adjusting said predetermined factor to obtain an accurate heart sound signal.

7. An apparatus for deriving a broad range of heart sounds from a patient comprising:
   a. a first acoustic sensor for placement at a predetermined location on the precordial region of the patient, said first acoustic sensor detecting thoracic sound waves and converting them into a first output electrical signal, variations in said first output electrical signal being a function of the sound waves;
   b. a second acoustic sensor for placement at a predetermined location on the axillary region of the patient, said second acoustic sensor detecting thoracic sound waves and converting them into a second output electrical signal, variations in said second output electrical signal being a function of the sound waves;

c. an acoustic transmitter for placement at a predetermined location on the axillary region of the patient opposite said second acoustic sensor, said acoustic transmitter transmitting sound waves of predetermined frequencies to the patient for electronic phase correction;

d. securement means which adjustably engages said first and said second acoustic sensors and said acoustic transmitter, and holds said sensors and said transmitter to their respective said predetermined locations on the patient;

e. electrical signal processing means communicatively connected to said first acoustic sensor, said second acoustic sensor and said acoustic transmitter, said electrical signal processing means having automatic amplification means for amplifying said second output electrical signal by a predetermined factor to produce an amplified output signal, subtraction means for subtraction of said amplified output signal from said first output electrical signal to produce a subtracted output signal, and phase correction means to compensate for electronic phase shifts in said first and said second acoustic sensors, said phase correction means comprising a microprocessor, an oscillator, a double pole-double throw switch, and a delay network, whereby said oscillator cycles through a range of frequencies selected by said microprocessor; said range of frequencies are fed into said acoustic transmitter to generate corresponding sound waves for transmission to the patient; said microprocessor detects which of said first or said second acoustic sensors first produces said first or said second output electrical signals respectively in response to said transmitted sound waves; said double pole-double throw switch, being controlled by said microprocessor, shunts the earlier produced output electrical signal to said delay network where the earlier produced output electrical signal is held for a predetermined time period, said predetermined time period being fixed by said microprocessor and further being dependent upon the phase difference between said first acoustic sensor and said second acoustic sensor; and the settings for said double pole-double throw switch and said delay network are maintained for subsequent phase correction of said first and second output electrical signals; and f. output means communicatively connected to said electrical signal processing means for displaying said subtracted output signal for operator diagnosis, whereby lung sound components of the input sound waves to said first and second acoustic sensors are cancelled.

8. The apparatus of claim 7, wherein said electrical signal processing means additionally has a pair of preamplifiers, each said preamplifier increasing the voltage of said first and said second output electrical signals by an equivalent fixed amount.

9. The apparatus of claim 7, wherein said amplification means is an adjustable gain amplifier variably setting said predetermined factor.

10. The apparatus of claim 7, wherein said amplification means is manually adjustable by an operator.

11. The apparatus of claim 7, wherein said amplification means is automatically adjustable by means of a microprocessor.

12. The apparatus of claim 7, wherein said subtraction means is a differential amplifier.

13. The apparatus of claim 7, wherein said output means comprises a cathode-ray tube visually displaying said subtracted output signal, a printer producing a hard copy of said subtracted output signal and headphone means for simultaneous aural monitoring of said subtracted output signal by the operator.

14. The apparatus of claim 7, wherein said first and said second acoustic sensors comprise microphones.

15. The apparatus of claim 7, wherein said first and said seconc acoustic sensors comprise:

a. a housing structure having an open end and retaining the remaining elements of the sensor and for reception of sound waves;

b. hydrophone means, placed within said housing structure, for producing electrical signals in response to transmitted thoracic bio-acoustic waves;

c. flexible diaphragm means, extended across said open end of said housing structure and having retention means to fix it thereto, for placement in direct contact with the patient; and d. a fluid medium filling the remaining interior volume of said housing structure and transmitting sound waves from said diaphragm means to said hydrophone means.

16. The apparatus of claim 7, wherein said acoustic transmitter comprises an electro-acoustic transducer.

17. The apparatus of claim 7, wherein said second acoustic sensor and said acoustic transmitter comprise bilateral transducers, whereby said second acoustic sensor is additionally usable for transmission of sound waves of predetermined frequencies to the patient for electronic phase correction, and said acoustic transmitter is additionally usable for detecting thoracic sound waves and for converting them into an output electrical signal, whereby said second acoustic sensor and said acoutic transmitter are interchangeable for use.

* * * * *